United States Patent [19]

Andrews

[11] 4,322,557

[45] Mar. 30, 1982

[54] 1-ARYLOXY-2-(S)-HYDROXY-3-(TRIARYL-PHOSPHONIO)-PROPANE DERIVATIVES AS PROSTAGLANDIN INTERMEDIATES

[75] Inventor: Glenn C. Andrews, Waterford, Conn.

[73] Assignee: Pfizer Inc., New York, N.Y.

[21] Appl. No.: 234,292

[22] Filed: Feb. 17, 1981

[51] Int. Cl.$^3$ ............................................... C07C 45/26
[52] U.S. Cl. ........................................... 568/11; 568/9
[58] Field of Search ...................................... 568/9, 11

[56] References Cited

U.S. PATENT DOCUMENTS

| | | | |
|---|---|---|---|
| 3,452,099 | 6/1969 | Grayson et al. | 568/11 |
| 3,689,601 | 9/1972 | Grayson et al. | 568/9 |
| 4,162,312 | 7/1979 | Brown | 568/11 |

OTHER PUBLICATIONS

*Organic Phosphorus Compounds* vol. 2 1973 Kosolapoff & Maier Wiley-Interscience, New York.
*Organophosphorus Compounds* 1951 Kosolapoff J. Wiley & Sons Inc., New York.
Corey et al., J.A.C.S. 93, 1490–1491 (1971).
Corey et al., Tetrahedron Letters 37, 3231–3234 (1977).
McLure et al., J.A.C.S. 10, 3666–3668 (1979).
Niwa et al., Chemistry Letters 1977, p. 1211–1214.

*Primary Examiner*—Winston A. Douglas
*Assistant Examiner*—Raymond K. Covington
*Attorney, Agent, or Firm*—Charles J. Knuth; Peter C. Richardson

[57] ABSTRACT

1-Aryloxy-2-(S)-hydroxy-3-(triarylphosphonio)-propane salts and alkali metal ylids thereof are novel intermediates useful in the direct synthesis of 15-(R)-hydroxy-16-aryloxy-prostaglandins.

9 Claims, No Drawings

1-ARYLOXY-2-(S)-HYDROXY-3-(TRIARYLPHOSPHONIO)-PROPANE DERIVATIVES AS PROSTAGLANDIN INTERMEDIATES

BACKGROUND OF THE INVENTION

The present invention relates to novel chiral intermediates useful for the synthesis of optically active prostaglandins.

15-Hydroxy-16-aryloxy-ω-tetranorprostaglandins are described in U.S. Pat. Nos. 4,087,604 and 4,157,341. As described therein, the synthesis of such compounds has included the reaction of an appropriate known 2-[5α-hydroxy-2β-formylcyclopent-1α-yl]acetic acid γ-lactone derivative (see Corey et al., J.A.C.S. 93, 1491 (1971); Tetrahedron Letters, 1971, 4753) with an appropriate dialkyl 2-ketophosphonate, reduction of the keto group to hydroxy and separation of the optical isomers of the resulting racemic mixture, followed by subsequent reaction steps to incorporate the upper prostaglandin side chain. The separation of the optical isomers in such a synthesis by chromatographic or other conventional methods is particularly difficult and there has been a need for other methods of synthesis to give the desired 15-R-hydroxy configuration in the resulting prostaglandin without the need for such separation method.

SUMMARY OF THE INVENTION

The present invention relates to novel intermediates useful in a chiral synthesis of 15-(R)-hydroxy-16-aryloxy-prostaglandins. The intermediates of the present invention are compounds of the formulae

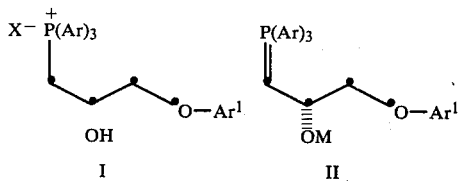

wherein Ar and $Ar^1$ are each phenyl or monosubstituted phenyl, said substituent being alkyl of 1 to 3 carbon atoms, alkoxy of 1 to 3 carbon atoms or fluoro; M is an alkali metal; and X is iodo, chloro, bromo, mesyl or tosyl. Preferably, Ar and $Ar^1$ are phenyl or p-fluorophenyl, most preferably phenyl, M is lithium, sodium or potassium, most preferably lithium, and X is iodo, tosyl or mesyl.

DETAILED DESCRIPTION OF THE INVENTION

The salts of formula I are readily prepared from (R)-2,3-0-isopropylidene-1-0-toluenesulfonyl-1,2,3-trihydroxypropane. Such starting materials may be prepared according to the procedure described by Baldwin et al. in J. Org. Chem. 43,4876 (1978), wherein the bisacetonide of D-mannitol is cleaved by reaction with lead tetraacetate followed by reduction, for example with an alkali metal borohydride such as sodium borohydride, to give (S)-glycerol-1,2-acetonide. Reaction with tosyl chloride in pyridine at about 0° C. produces the desired starting material.

The (R)-2,3-O-isopropylidene-1-O-toluenesulfonyl-1,2,3-trihydroxypropane is reacted with an appropriately substituted phenol of the formula $Ar^1OH$ in the presence of a base, for example an alkali metal hydroxide or carbonate, and an alkali metal halide, such as a sodium or potassium halide, especially sodium or potassium iodide. The reaction is generally conducted in an organic solvent such as dimethylformamide, at a temperature from about 75° C. to about 125° C., preferably from about 100° C. to 120° C., preferably under a nitrogen atmosphere. The (R)-1-aryl-2,3-isopropylidene-1,2,3-trihydroxypropane formed by this reaction is then heated with an acid, for example an aqueous mineral acid such as hydrochloric acid or sulfuric acid at a temperature from about 40° C. to about 80° C., in an aqueous solution of a water-miscible organic solvent, such as tetrahydrofuran, dimethylformamide, acetone and the like, preferably at reflux temperature in acetone, to remove the hydroxyl protecting group. Reaction of the formed (R)-1-aryloxy-2,3-dihydroxypropane with tosyl or mesyl chloride in a basic organic solvent such as pyridine, or in an organic solvent such as ether, ethyl acetate and the like in the presence of a base such as a trialkylamine, for example triethylamine, at a temperature from about −25° C. to 10° C., preferably about −20° C. to −10° C. forms (S)-1-O-tosyl-3-aryloxy-1,2-dihydroxypropane, or the mesyl analog thereof. Reaction of the tosyl- or mesyl- substituted compounds with an alkali metal halide in a polar, aprotic organic solvent, for example dimethylformamide, dimethylsulfoxide, or a dialkyl ketone having from 1 to 3 carbon atoms in each alkyl group, preferably acetone, at a temperature from about 10° C. to 40° C., preferably about 20° C. to 30° C., yields an (S)-1-halo-3-aryloxy-2-hydroxypropane. Preferably, this reaction is effected with an alkali metal iodide under dark conditions.

Reaction of either the tosyl-, mesyl-, or halo substituted-3-aryloxy-2-hydroxypropane compounds described above with an appropriate triarylphosphine of the formula $(Ar)_3P$ in an organic solvent such as an aromatic hydrocarbon, for example benzene, toluene, xylene, or, preferably, in sulfolane, at a temperature from about 40° C. to about 100° C., preferably about 55° C. to 75° C., preferably under nitrogen, yields the desired compound of formula I.

An alternative method of preparation of the salts of formula I is from (S)-epichlorhydrin, which on reaction with an alkali metal aryloxide in an alcohol solvent such as methanol, forms the corresponding (R)-glycidol aryl ether, see Hunsberger et al., Chem. Ind. volume 88, (1959), and McLure et al., J.A.C.S. 101, 3666 (1979). Reaction with a halotrialkylsilane, for example iodo- or chlorotrimethylsilane in the presence of a triarylphosphine catalyst, preferably triphenylphosphine, in a solvent such as chloroform at a temperature from about 10° C. to 60° C., preferably about 20° C. to 35° C., to form a 1-halo-2-O-trimethylsilyl-3-aryloxypropane. Hydrolysis of the latter by heating in the presence of an acid, for example a mineral acid, such as hydrochloric acid, or an organic acid such as aqueous acetic acid, at a temperature from about 50° C. to about 100° C. yields the corresponding 1-halo-2-hydroxy-3-aryloxypropane, which is readily converted to the desired salt of formula I by reaction with a triarylphosphine, as previously described.

If desired, a salt of formula I obtained by the procedures described above may be used to prepare other such salts having different counterions. For example, the salt may be passed over an anion exchange resin having the desired counterion, or be contacted with an excess of an appropriate acid.

The ylids of formula II are formed by the reaction of the salt of formula I with an alkali metal alkyl, for example n-butyllithium, or analogous sodium or potassium alkyls. In this manner the ylid may be conveniently generated in situ for subsequent reaction with an appropriate formyl-substituted-cyclopentane derivative of formula III, known in the art as a precursor for prostaglandins, in accord with the following reaction scheme:

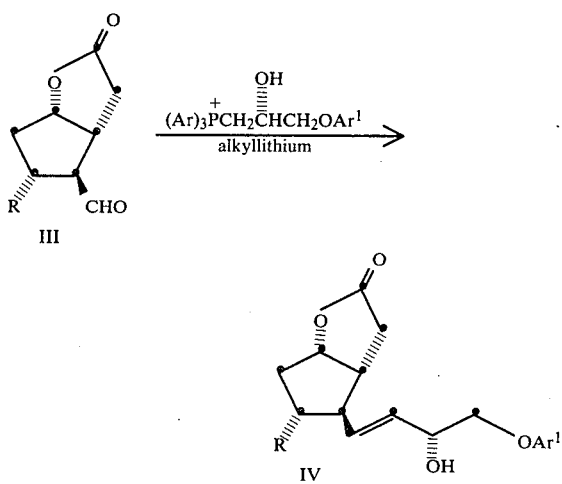

where R is hydrogen or —OR', where R' is a base-stable hydroxyl-protecting group, such as tetrahydropyranyl, trialkylsilyl, phenylbenzoyl, and the like.

The compounds of formula IV are known in the art and are useful as prostaglandin intermediates. In particular, they may be converted to 15-(R)-hydroxy-16-aryloxy-prostaglandins by methods known in the art, as described, for example, in U.S. Pat. Nos. 4,087,604 and 4,157,341. However, it will be understood that such intermediates will also be useful in the preparation of other 16-aryloxyprostaglandins having differing upper side chains, for example, having various chain lengths, $C_1$ substituents and degrees of unsaturation therein. The 15-(R)-hydroxy-16-aryloxy prostaglandins produced are useful as therapeutic agents, having activity, for example, as antiulcer agents, antihypertensive agents, bronchodilators and as antifertility agents and abortifacients.

The present invention is illustrated by the following examples. However, the invention is not limited to the specific details of these examples. All temperatures are in degrees centigrade.

EXAMPLE 1

(R)-1-phenoxy-2,3-dihydroxypropane

A mixture of 110 g (0.384 mol) of (R)-2,3-O-isopropylidene-1-O-tuluenesulfonyl-1,2,3-trihydroxypropane (J. J. Baldwin, A. W. Raab, K. Mensler, B. H. Arison, D. E. McClure, *J. Org. Chem.*, 43, 4876 (1978)), 72.3 g (0.768 mol) of phenol, 106.2 g (0.768 mol) of potassium carbonate, and 1.0 g (0.007 mole) of potassium iodide in 400 ml of dry dimethylformamide was heated under nitrogen at 100°-110° for 5 hours. After cooling to room temperature, 600 ml of ether was added, the slurry filtered and the filtrate washed with water, brine, and dried over anhydrous magnesium sulfate. Removal of the drying agent by filtration followed by isolation in vacuo afforded an oil which was refluxed in 80 ml of acetone and 240 ml of 1N hydrochloric acid for 30 minutes. The acetone was removed in vacuo, the aqueous solution extracted with 3×200 ml of ethyl acetate and the combined organic layers washed with 1N sodium hydroxide (200 ml), water (200 ml), brine (200 ml) and dried over anhydrous magnesium sulfate. On removal of the drying agent by filtration the solvent was removed in vacuo to afford an oil, which solidified on standing. Crystallization from ethyl acetate/petroleum ether afforded 29.8 g (51%) of the title compound: mp 64°-65°; $[\alpha]_{24}^D$ −8.88° (1,.5,CHCl$_3$); $^1$H-nmr (CDCl$_3$) δ 7.50-6.81 (m,5), 4.31-3.89 (m,1), 4.01 (s,2,O$\underline{H}$), 3.89-3.57 (m,4); ir (KBr) cm$^{-1}$ 3425 (s,OH).

A second crop afforded an additional 4.4 g (8%), for a combined yield of 59%.

EXAMPLE 2

(S)-1-O-p-Toluenesulfonyl-3-phenoxy-1,2-dihydroxypropane

To a cold (−15°) solution of 30 g (0.20 mol) of (R)-1-phenoxy-2,3-dihydroxypropane in 90 ml of pyridine was added 37.9 g (0.2 mol) of p-toluene-sulfonylchloride. The reaction mixture was allowed to stir at −10° an additional hour. 500 ml of ether was added, and the mixture was washed successively with 500 ml of water, 500 ml 1N hydrochloric acid, 200 ml of water, 200 ml of brine and dried over anhydrous magnesium sulfate. Removal of the drying agent by filtration followed by isolation in vacuo afforded 60 g (91%) of an oil shown by $^1$H-nmr to be the title compound, containing 15% of the di-tosylate.

The oil was used in the following example without further purification:

$^1$H-nmr (CDCl$_3$)δ 7.98-7.60 (m,2), 7.46-6.50 (m,7), 4.34-3.83 (m,5), 2.63 (s,1,O-$\underline{H}$), 2.35 (s,3).

EXAMPLE 3

(S)-1-Iodo-3-phenoxy-2-hydroxypropane

A mixture of 60 g (0.18 mol) (S)-1-O-p-Toluenesulfonyl-3-phenoxy-1,2-dihydroxypropane, 108 g (0.72 mol) of sodium iodide in 1.2 liters of acetone was stirred in the dark for 6 days at 25°. The slurry was stripped to a solid, 1.5 l of chloroform added, the organic layer was washed with 0.5 l of 10% aqueous sodium thiosulfate, followed by brine and dried over anhydrous magnesium sulfate. The drying agent was removed by filtration and the filtrate stripped in vacuo to an oil comprising 36.0 g:

$^1$H-nmr (CDCl$_3$)δ 7.43-6.65 (m, 5H), 3.94 (m, 3H), 3.28 (d, 2H), 2.86 (s, 1H); $^{13}$C-nmr (CDCl$_3$ assigned 76.95δ) δ 157.8 (s), 129.3 (d), 121.1 (d), 114.4 (d), 70.2 (t, -$\underline{C}$H$_2$-O-), 69.2

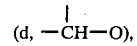
(d, —CH—O), 9.3 (t, -$\underline{C}$H$_2$I); mass spectrum (70 eV) m/e 278.9812 (parent, C$_9$H$_{11}$O$_2$I); ir (film) δ 3333 (s,OH). The crude oil was used without further purification in the following example.

EXAMPLE 4

1-Phenoxy-2-(S)-hydroxy-3-(triphenylphosphonio)-propane iodide

A mixture of 36.0 g (0.13 mole) of (S)-1-iodo-3-phenoxy-2-hydroxypropane, 34.1 g (0.13 mol) of triphenylphosphine in 100 ml of dry sulfolane was stirred in the dark under a nitrogen atmosphere at 60° for 5 days, whereupon was added 200 ml of chloroform followed by 800 ml of ether. The precipitated oil was removed from the solvent by decantation, redissolved in 50 ml of chloroform and reprecipitated by the addition of 450 ml of ether. This procedure was repeated 4 times and the resulting oil dried under vacuum overnight affording 26.0 g (37%) of a friable foam shown by $^1$H-nmr to be a 1:1 complex of the title compound with sulfolane: $^1$H-nmr (CDCl$_3$) δ 8.00-6.74 (m, 23); 4.50-3.60 (m,6); $^{13}$C-nmr (CDCl$_3$, assigned 76.95δ) δ 157.1, 113.9, 128.7, 120.3 (C$_6$H$_5$O), 117.7 (d, J$_{cp}$=86.9 Hz), 134.2 (d, J$_{cp}$=2.1 Hz), 133.0 (d, J$_{cp}$=10.3 Hz), 129.5 (d, J$_{cp}$=13 Hz), 70.20 (d, J$_{cp}$=13.9 Hz, -CH$_2$-O Arom), 64.0

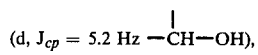

(d, J$_{cp}$ = 5.2 Hz —CH—OH), 27.8 (d, J$_{cp}$=54.5 Hz, -H$_2$CP$^{32}$).

EXAMPLE 5

(S)-1-Chloro-2-O-trimethylsilyl-3-phenoxypropane

To a stirred solution of 38 g (0.35 mol) of chlorotrimethylsilane and (R)-glycidol phenyl ether, (prepared by the reaction of potassium carbonate, phenol and S-epichlorohydrin in acetone, see McLure et al., J.A.C.S. 101, 3666 (1979)) in 200 ml of ethanol free chloroform is added 0.9 g (3.4 mmol) of triphenylphosphine catalyst. The mixture is cooled and is stirred at ambient temperature for 30 minutes. The solvent is removed in vacuo to afford the title trimethylsilyl ether:

EXAMPLE 6

(S)-1-Chloro-2-hydroxy-3-phenoxypropane

A mixture of 77.0 g (0.3 mol) of 1-chloro-2-O-trimethylsilyl-3-phenoxypropane, 50 ml of glacial acetic acid, and 50 ml of water in 200 ml of tetrahydrofuran is heated at 60° under a nitrogen atmosphere for 2 hours. On removal of solvent in vacuo the residue is taken up in chloroform, washed with saturated aqueous sodium bicarbate and dried over anhydrous sodium sulfate. Removal of the solvent in vacuo affords the title compound.

EXAMPLE 7

(S)-1-Iodo-2-hydroxy-3-phenoxypropane

A mixture of 55 g (0.29 mol) of 1-chloro-2-hydroxy-3-phenoxypropane, 170 g (1.1 mol) sodium iodide in 1.0 of acetone is refluxed in the dark under a nitrogen atmosphere for 3 days. The acetone is removed in vacuo, the residue slurried in chloroform, filtered and the filtrate stripped to afford the title compound.

EXAMPLE 8

(S)-1-Iodo-2-hydroxy-3-phenoxypropane

To a rapidly stirring, cooled (ice water bath) mixture of 37.5 g (0.25 mol) of R-glycidol phenyl ether and 0.655 g (2.5 mmol) of triphenylphosphine in 200 ml of ethanol free chloroform is added slowly via a syringe 50 g (0.250 mol) of iodotrimethylsilane. The chloroform is washed with 200 ml of 10% aqueous sodium thiosulfate, brine, and dried over magnesium sulfate. Isolation in vacuo affords the title compound.

EXAMPLE 9

1-4[4-phenoxy-3,R-hydroxy-1,E-butenyl]-5-[(t-butyldimethylsilyl)oxy]-3,r,-3a,4,5,6,6a-hexahydro-2H-cyclopenta-(b)-furan-2-one To a solution of 3.3 g (6.1 mmol) of 1-phenoxy-2-(S)-hydroxy-3-(triphenylphosphonio)-propane iodide in 25 ml of dry tetrahydrofuran at −78° under an argon atmosphere was added via syringe 3.8 ml (6.1 mmol) of 1.6 M n-butyllithium in hexane over a period of 13 minutes followed by 4.7 ml (6.1 mmol) of 1.3 M sec-butyllithium in cyclohexane over a one minute period. The anion was stirred at −78° for 30 minutes followed by the addition of 2.14 g (6.1 mmol) of 1-4-formyl-5[(t-butyldimethylsilyl)oxy]-3, -3a,4,5,6,6a-hexahydro-2H-cyclopenta-(b)-furan-2-one in 20 ml of tetrahydrofuran over 3 minutes. The solution was stirred for 1 hour at −78°, allowed to come to ambient temperature, stirred an additional 30 minutes, and quenched by the addition of 30 ml of pH 4 sodium citrate buffer. The organic layer was separated, the aqueous layer extracted with ethyl acetate and the combined organic layers washed with water, brine and dried over anhydrous magnesium sulfate. Removal of the drying agent followed by isolation in vacuo afforded 4.8 g of an oil which was chromatographed on 100 g of silica gel using 1:11 ethyl acetate-hexane to afford the title compound as an oil, homogeneous by TLC and shown by HPLC analysis to be the desired pure R alcohol uncontaminated by the epimeric S compound: [α]$_{20}$$^D$-20.7 (CHCl$_3$,2); mass spectrum m/e (70 eV) 361 (parent-C$_4$H$_9$, base) 343 (-H$_2$O), 105 (-S: C$_{16}$H$_{15}$); $^1$H-nmr(CDCl$_3$)δ 7.55-6.90 (m,5H), 6.02 (m,1,=CH-), 5.88 (m,1,=CH), 5.00 (m,1,-CH-O-C-), 4.62 (m,1,CH-OH), 4.30-3.85 (m,3), 3.0-2.0 (m,6), 1.00 (s,9), 0.15 (s,6).

EXAMPLE 10

1-4[4-phenoxy-3,R-hydroxy-1,E-butenyl]-5-(p-phenylbenzoyl)-3,r,-3a,4,5,6,6a-hexahydro-2H-cyclopenta-(b)-furan-2-one Following the procedure of Example 9, 3.3 g (6.1 mmol) of 1-phenoxy-2-(S)-hydroxy-3-(triphenylphosphonio)-propane iodide was treated successively with 3.8 ml (6.1 mmol) of n-butyllithium, 4.7 ml (6.1 mmol) of sec-butyllithium and 2.14 g (6.1 mmol) of 1-4-formyl-5(p-phenylbenzoyl)-3,r-3a,4,5,6,6a-hexahydro-2H-cyclopenta-(b)-furan-2-one. Workup as in Example 9 afforded 4.0 g of an oil, which was chromatographed on 100 g of silica gel using 95:5 chloroform/methanol as eluant to afford 80 mg of pure S alcohol as evidenced by TLC and HPLC analysis and comparison with authentic material: $^1$H-nmr (CDCl$_3$)δ 8.10-6.65 (m,14), 5.68 (m,2), 5.05 (m,3), 4.38 (m,1), 3.82 (AB,2), 3.75 (s,1,OH) 3.0-2.0 (m,6); mass spectrum (70 eV) m/e 286.4 (parent-p-phenylbenzoyl); ir (CHCl$_3$, 1%), cm$^{-1}$350 (m,OH), 1773

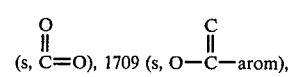

(s, C=O), 1709 (s, O—C—arom), 1681 (m, C=C, trans), 967 (m, C=C, trans).

I claim:
1. A compound of the formula

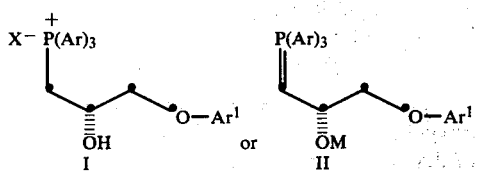

having the 2-(S)-configuration, wherein Ar and $Ar^1$ are each phenyl or monosubstituted phenyl, said substituent being alkyl of 1 to 3 carbon atoms, alkoxy of 1 to 3 carbon atoms or fluoro; M is an alkali metal; and X is iodo, chloro, bromo, mesyl or tosyl.

2. A compound of claim 1, formula I.
3. A compound of claim 2 wherein $Ar^1$ is phenyl or p-fluorophenyl.
4. A compound of claim 2 wherein Ar and $Ar^1$ are each phenyl.
5. A compound of claim 4 wherein X is iodo, mesyl or tosyl.
6. A compound of claim 1, formula II.
7. A compound of claim 6 wherein $Ar^1$ is phenyl or p-fluorophenyl and M is lithium, sodium or potassium.
8. A compound of claim 7 wherein Ar and $Ar^1$ are each phenyl.
9. A compound of claim 8 wherein M is lithium.

* * * * *